US00PP32598P3

(12) United States Plant Patent
Moen

(10) Patent No.: US PP32,598 P3
(45) Date of Patent: Dec. 8, 2020

(54) *GERBERA* PLANT NAMED 'SWEET FROSTING'

(50) Latin Name: *Gerbera hybrida*
Varietal Denomination: Sweet Frosting

(71) Applicant: HilverdaFlorist B.V., Aalsmeer (NL)

(72) Inventor: Melchior Moen, Mijdrecht (NL)

(73) Assignee: HILVERDA FLORIST B.V., De Kwakel (NL)

( * ) Notice: Subject to any disclaimer, the term of this patent is extended or adjusted under 35 U.S.C. 154(b) by 0 days.

(21) Appl. No.: 16/873,401

(22) Filed: Apr. 4, 2020

(65) Prior Publication Data

US 2020/0329604 P1 Oct. 15, 2020

Related U.S. Application Data

(60) Provisional application No. 62/920,012, filed on Apr. 9, 2019.

(51) Int. Cl.
*A01H 5/02* (2018.01)
*A01H 6/14* (2018.01)

(52) U.S. Cl.
USPC ..... Plt./357
CPC ..... *A01H 6/1456* (2018.05)

(58) Field of Classification Search
USPC ..... Plt./357
CPC ..... A01H 6/1456
See application file for complete search history.

(56) References Cited

PUBLICATIONS

UPOV hit for a *Gerbera* plant named, 'Sweet Frosting', QZ PBR 20183033, filed Nov. 20, 2018.*

* cited by examiner

*Primary Examiner* — Anne Marie Grunberg
(74) *Attorney, Agent, or Firm* — C. Anne Whealy

(57) ABSTRACT

A new and distinct cultivar of *Gerbera* plant named 'Sweet Frosting', characterized by its compact, broadly upright and uniformly mounding plant habit; dense and bushy appearance; numerous inflorescences with white-colored ray florets; upright and moderately strong scapes; and good garden performance and relative tolerance to high and low temperatures.

1 Drawing Sheet

Botanical designation: *Gerbera hybrida.*
Cultivar denomination: 'SWEET FROSTING'.

BACKGROUND OF THE INVENTION

The present invention relates to a new and distinct cultivar of *Gerbera* plant, botanically known as *Gerbera hybrida* and hereinafter referred to by the cultivar name 'Sweet Frosting'.

The new *Gerbera* plant is a product of a planned breeding program conducted by the Inventor in De Kwakel, The Netherlands. The objective of the breeding program is to create new compact garden *Gerbera* plants with numerous attractive inflorescences, resistant to cold temperatures and good garden performance.

The new *Gerbera* plant originated from a cross-pollination in March, 2012 of a proprietary selection of *Gerbera hybrida* identified as code number 10T0350, not patented, as the female, or seed, parent with a proprietary selection of *Gerbera hybrida* identified as code number 11T0730, not patented, as the male, or pollen, parent. The new *Gerbera* plant was discovered and selected as a single flowering plant from within the progeny of the stated cross-pollination in a controlled greenhouse environment in De Kwakel, The Netherlands in June, 2013.

Asexual reproduction of the new *Gerbera* plant by vegetative terminal cuttings and in vitro meristem culture since June, 2014 has shown that the unique features of this new

*Gerbera* plant are stable and reproduced true to type in successive generations of asexual reproduction.

SUMMARY OF THE INVENTION

Plants of the new *Gerbera* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'Sweet Frosting'. These characteristics in combination distinguish 'Sweet Frosting' as a new and distinct *Gerbera* plant:

1. Compact, broadly upright and uniformly mounding plant habit.
2. Dense and bushy appearance.
3. Numerous inflorescences with white-colored ray florets.
4. Upright and moderately strong scapes.
5. Good garden performance and relative tolerance to high and low temperatures.

Plants of the new *Gerbera* differ primarily from plants of the female parent selection in the following characteristics:

1. Plants of the new *Gerbera* have narrower leaves than plants of the female parent selection.

2. Plants of the new *Gerbera* have smaller inflorescences than plants of the female parent selection.
3. Plants of the new *Gerbera* have shorter scapes than plants of the female parent selection.

Plants of the new *Gerbera* differ primarily from plants of the male parent selection in inflorescence size as plants of the new *Gerbera* have larger inflorescences than plants of the male parent selection. In addition, scapes of plants of the new *Gerbera* are mostly green in color whereas scapes of plants of the male parent selection are reddish green in color.

Plants of the new *Gerbera* can be compared to plants of the *Gerbera hybrida* 'Garsylvana', disclosed in U.S. Plant Pat. No. 22,442. Plants of the new *Gerbera* differ from plants of 'Garsylvana' in the following characteristics:

1. Plants of the new *Gerbera* have larger inflorescences than plants of 'Garsylvana'.
2. Inflorescences of plants of the new *Gerbera* have darker-colored centers than inflorescences of plants of 'Garsylvana'.

BRIEF DESCRIPTION OF THE PHOTOGRAPH

The accompanying photograph illustrates the overall appearance of the new *Gerbera* plant showing the colors as true as it is reasonably possible to obtain in colored reproductions of this type. Colors in the photograph may differ slightly from the color values cited in the detailed botanical description which accurately describe the colors of the new *Gerbera* plant.

The photograph is a side perspective view of a typical flowering plant of 'Sweet Frosting' grown in a container.

DETAILED BOTANICAL DESCRIPTION

The aforementioned photograph and following observations and measurements describe plants grown during the spring and summer in 17-cm containers in a glass-covered greenhouse in De Kwakel, The Netherlands and under cultural practices typical of commercial garden *Gerbera* production. During the production of the plants, day temperatures ranged from 12° C. to 18° C. and night temperatures ranged from 12° C. to 16° C. Plants were six months old when the photograph was taken and 20 weeks old when the description was taken. In the following description, color references are made to The Royal Horticultural Society Colour Chart, 2015 Edition, except where general terms of ordinary dictionary significance are used.

Botanical classification: *Gerbera hybrida* 'Sweet Frosting'.

Parentage:

*Female, or seed, parent.*—Proprietary selection of *Gerbera hybrida* identified as code number 10T0350, not patented.

*Male, or pollen, parent.*—Proprietary selection of *Gerbera hybrida* identified as code number 11T0730, not patented.

Propagation:

*Type.*—By cuttings and in vitro meristem culture.

*Time to initiate roots, by cuttings, summer and winter.*—About 3.5 weeks at minimum temperatures of 20° C.

*Time to initiate roots, by tissue culture, summer and winter.*—About 2.5 to 3 weeks at minimum temperatures of 20° C.

*Time to produce a rooted young plant, by cuttings, summer and winter.*—About 3.5 weeks at temperatures about 20° C. to 26° C.

*Time to produce a rooted young plant, by tissue culture, summer and winter.*—About five to six weeks at temperatures about 20° C.

*Root description.*—Fibrous; typically white in color, actual color of the roots is dependent on substrate composition, water quality, fertilizer type and formulation, substrate temperature and physiological age of roots.

Plant description:

*Appearance.*—Herbaceous perennial that is typically grown as a container or garden plant; compact and uniformly mounding plant habit; upright, broadly spreading and roughly flattened globular in shape; numerous leaves arranged in basal rosettes; dense and bushy habit; inflorescences held above the foliar plane on erect and strong basal scapes; moderately vigorous growth habit and moderate growth rate.

*Plant height, soil level to top of foliar plane.*—About 20 cm.

*Plant height, soil level to top of inflorescences.*—About 44.9 cm.

*Plant width or spread.*—About 35.4 cm.

Leaf description:

*Arrangement.*—Alternate, basal, simple.

*Length.*—About 11.7 cm.

*Width.*—About 7.8 cm.

*Shape.*—Ovate; slightly to moderately concave.

*Apex.*—Obtuse.

*Base.*—Hastate to shallowly sagittate and tapering at the base.

*Margin.*—Coarsely and irregularly angulate; slightly to moderately undulate.

*Texture and luster, upper surface.*—Moderately to densely pubescent; slightly rugose; moderately glossy.

*Texture and luster, lower surface.*—Moderately to densely pubescent, slightly rugose; slightly glossy.

*Venation pattern.*—Pinnate.

*Color.*—Developing leaves, upper surface: Close to between 141A and 143A. Developing leaves, lower surface: Close to 146B. Fully expanded leaves, upper surface: Slightly darker than NN137A; venation, close to 143C. Fully expanded leaves, lower surface: Close to 147B; venation, close to 146B to 146C.

*Petioles.*—Length: About 9.9 cm. Diameter: About 3 mm. Texture and luster, upper and lower surfaces: Densely pubescent; moderately glossy. Strength: Moderate to strong. Color, upper surface: Close to 143A; proximally, close to 146B. Color, lower surface: Close to 144A; proximally tinged with close to 197A.

Inflorescence description:

*Appearance.*—Composite inflorescence form with oblanceolate-shaped ray florets; solitary inflorescences borne on upright and moderately strong scapes and held above the foliar plane; ray and disc florets arranged acropetally on a capitulum; inflorescences face upright.

*Fragrance.*—None detected.

*Flowering season.*—Plants begin flowering about three months after planting; under garden conditions in The Netherlands, plants flower from spring to late autumn; plants can be flowered year-round in the greenhouse.

*Inflorescence longevity.*—Depending on the temperature, inflorescences last about three weeks on the plant; inflorescences persistent.

*Quantity of inflorescences.*—Freely flowering habit with about ten open inflorescences per plant at one time.

*Inflorescence buds.*—Height: About 2.5 cm. Diameter: About 1.8 cm. Shape: Broadly oblong. Texture and luster: Moderately pubescent; matte. Color: Close to 137C and distally, close to 143C; immature ray florets, close to between 145D and 157B.

*Inflorescence size.*—Diameter: About 7.2 cm. Depth (height): About 3.2 cm. Diameter of disc: About 2.2 cm.

*Receptacles.*—Height: About 2 mm. Diameter: About 4.5 mm. Shape: Broadly rhomboidal. Color: Close to 157C.

*Ray florets.*—Quantity and arrangement: About 54 per inflorescence arranged in about three whorls. Orientation: Proximally, about 30° from vertical; distally, close to horizontal. Length: About 4.1 cm. Width: About 6 mm. Shape: Oblanceolate. Apex: Bluntly acute to narrowly obtuse. Base: Narrowly cuneate. Margin: Entire. Texture and luster, upper surface: Smooth, glabrous; velvety; matte. Texture and luster, lower surface: Smooth, glabrous; moderately velvety; slightly carinate; slightly glossy. Color: When opening, upper and lower surfaces: Close to NN155B. Fully opened, upper surface: Close to NN155C; at the apex, close to 157A; venation, close to NN155C; color does not change with development. Fully opened, lower surface: Close to NN155C; at the apex, close to 150D; venation, close to NN155C; color does not change with development.

*Disc florets.*—Quantity and arrangement: About 300 disc florets at center of the inflorescence arranged in a ten-whorl spiral. Length: About 1.6 cm. Width: About 3.5 mm. Shape: Tubular with one or two narrow free lobes and one broader free lobe. Apex: Acute and recurved; upper 15%, free. Base: Lower 85%, fused. Margin, free lobes: Entire. Texture, upper surface: Smooth, glabrous; moderately velvety; matte. Texture, lower surface: Smooth, glabrous; slightly velvety; slightly glossy. Color: When opening, inner and outer surface: Close to 11A; proximally, close to 4D. Fully opened, inner and outer surface: Close to 10D; proximally, close to 4D; color does not change with development.

*Pappus.*—Quantity of hairs per floret: About 60. Length: About 7 mm. Diameter: Less than 1 mm. Texture and luster: Soft; matte. Color: Close to 162D; distally, close to N77D.

*Phyllaries.*—Quantity and arrangement: About 60 per inflorescence arranged in about three whorls. Length: About 1.3 cm. Width (at base): About 2.5 mm. Shape: Ligulate. Apex: Narrowly acute. Base: Cuneate. Margin: Entire. Texture and luster, upper surface: Smooth, glabrous; moderately glossy. Texture and luster, lower surface: Densely pubescent; matte. Color, upper surface: Close to 143A; at the margins, close to 145D. Color, lower surface: Close to 137B.

*Scapes.*—Length: About 36.6 cm. Diameter: Proximally, about 5 mm; distally, about 4 mm. Strength: Moderately strong. Angle: About 15° from vertical. Texture and luster: Densely pubescent; moderately glossy. Color: Close to 144A; proximally, tinged with close to 178A; distally, close to 146B.

*Reproductive organs.*—Androecium (present on disc florets only): Quantity per floret: Five. Filament length: About 6 mm. Filament color: Close to 157D. Anther shape: Ligulate; basifixed. Anther size: About 4 mm by 0.3 mm. Anther color: Close to 13B. Pollen amount: Scarce to moderate. Pollen color: Close to 13B. Gynoecium (present only on ray and disc florets): Quantity per floret: One. Pistil length: About 1.2 cm. Stigma diameter: About 0.5 mm. Stigma shape: Cleft. Stigma color: Close to N77A. Style length: About 1.1 cm. Style color: Close to NN155C. Ovary color: Close to 157D.

*Seeds and fruits.*—To date, seed and fruit production has not been observed on plants of the new *Gerbera*.

Pathogen & pest resistance: Resistance to pathogens and pests common to *Gerbera* plants has not been observed on plants of the new *Gerbera* grown under commercial production conditions to date.

Garden performance: Plants of the new *Gerbera* have been observed to have good garden performance and to tolerate high temperatures about 35° C. and to be cold hardy to USDA Hardiness Zone 8.

It is claimed:

1. A new and distinct *Gerbera* plant named 'Sweet Frosting' as illustrated and described.

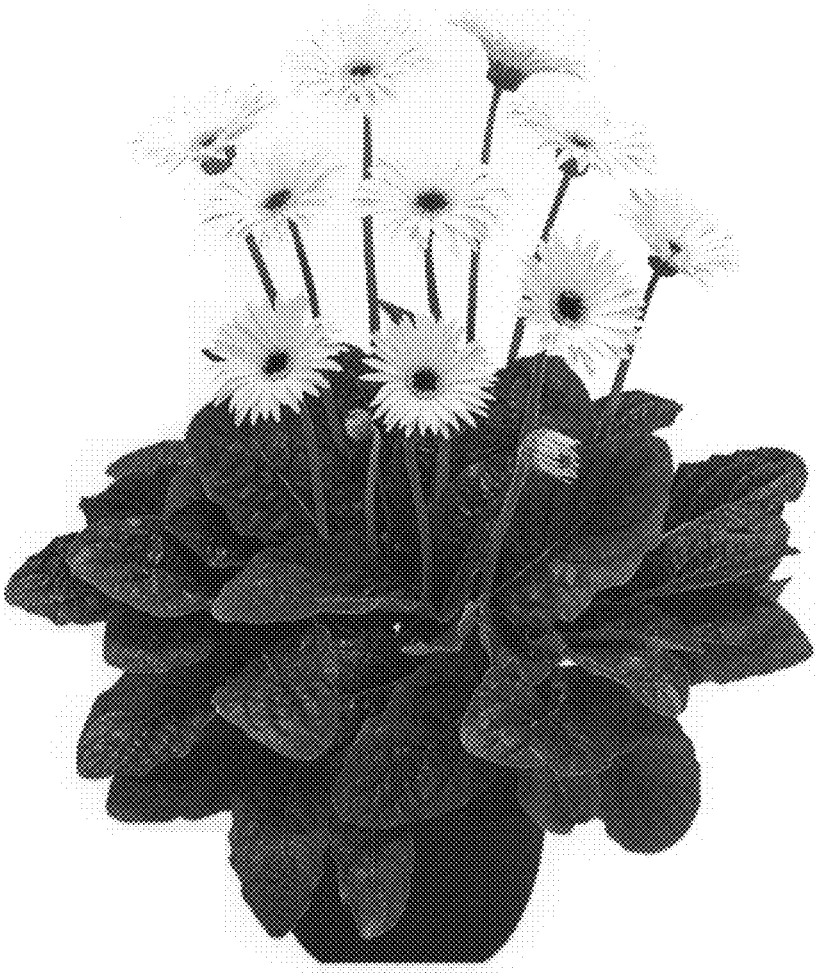

* * * * *